United States Patent [19]

Haunschild et al.

[11] Patent Number: 4,690,681
[45] Date of Patent: Sep. 1, 1987

[54] DISPOSABLE LEAKPROOF CATAMENIAL DEVICE

[75] Inventors: Susan M. Haunschild, Neenah; Stephen S. Hata, Menasha; Shirlee A. Wismer, Neenah, all of Wis.

[73] Assignee: Kimberly-Clark Corporation, Neenah, Wis.

[21] Appl. No.: 821,631

[22] Filed: Jan. 23, 1986

[51] Int. Cl.$^4$ .............................................. A61F 13/16
[52] U.S. Cl. ..................................................... 604/396
[58] Field of Search .................. 604/385.1, 385.2, 386, 604/387, 396, 397

[56] References Cited

U.S. PATENT DOCUMENTS

| | | |
|---|---|---|
| 272,190 | 1/1884 | Sneider . |
| 1,914,596 | 6/1933 | Diehl . |
| 1,929,363 | 10/1933 | Long . |
| 2,102,359 | 12/1937 | Frieman ............................. 604/396 |
| 2,206,412 | 7/1940 | Levy . |
| 2,299,446 | 10/1942 | White . |
| 2,748,772 | 6/1956 | Titone et al. . |
| 2,852,026 | 9/1958 | Karr . |
| 2,890,700 | 6/1959 | Holm ............................. 604/390 X |
| 2,964,039 | 12/1960 | Johnson, Jr. et al. . |
| 3,038,474 | 6/1962 | Harwood et al. . |
| 3,344,789 | 10/1967 | Arnold et al. . |
| 3,397,696 | 8/1968 | Richard . |
| 3,424,162 | 1/1969 | Parravicini . |
| 3,489,149 | 1/1970 | Larson . |
| 3,599,638 | 8/1971 | Rickard ............................. 604/396 |
| 3,599,640 | 8/1971 | Larson . |
| 3,608,551 | 9/1971 | Seijo . |
| 3,687,141 | 8/1972 | Matsuda . |
| 3,771,524 | 11/1973 | Ralph . |
| 3,805,790 | 4/1974 | Kaczmarzyk et al. ............ 604/387 |
| 4,031,568 | 6/1977 | Huff . |
| 4,044,769 | 8/1977 | Papajohn . |
| 4,059,114 | 11/1977 | Richards . |
| 4,067,068 | 1/1978 | Bregstein et al. . |
| 4,205,679 | 6/1980 | Repke et al. . |
| 4,244,059 | 1/1981 | Pflaumer . |
| 4,324,246 | 4/1982 | Mullane et al. . |
| 4,327,732 | 5/1982 | Thinnes . |
| 4,333,466 | 6/1982 | Matthews . |
| 4,355,425 | 10/1982 | Jones et al. . |
| 4,407,284 | 10/1983 | Pieniak ............................. 604/385 |
| 4,536,181 | 8/1985 | Cook ............................. 604/387 |
| 4,555,244 | 11/1985 | Buell ............................. 604/392 |
| 4,555,245 | 11/1985 | Armbruster ..................... 604/396 |
| 4,560,381 | 12/1985 | Southwell ....................... 604/396 |

FOREIGN PATENT DOCUMENTS

| | | |
|---|---|---|
| 0140471 | 5/1985 | European Pat. Off. . |
| 1062550 | 3/1967 | United Kingdom . |
| 1144674 | 3/1969 | United Kingdom . |
| 1342022 | 12/1973 | United Kingdom . |
| 1356465 | 6/1974 | United Kingdom . |
| 1520740 | 8/1978 | United Kingdom . |
| 2048684 | 12/1980 | United Kingdom . |
| 2112267 | 7/1983 | United Kingdom . |
| 2112268 | 7/1983 | United Kingdom . |
| 2124072 | 2/1984 | United Kingdom . |
| 2169489 | 7/1986 | United Kingdom . |
| 2169789 | 7/1986 | United Kingdom . |
| 2170394 | 8/1986 | United Kingdom . |

OTHER PUBLICATIONS

"U.K. Search Report of Feb. 19, 1987 in British Application 8701517".

Primary Examiner—John D. Yasko
Attorney, Agent, or Firm—Paul A. Leipold; Donald L. Traut; Jeremiah J. Duggan

[57] ABSTRACT

The invention is generally accomplished by providing a panty-like garment containing an integral menstrual pad. The absorbent pad portion extends from the crotch region up in both the back and the front to a point higher than normal menstrual pads. The pad extends at least up to the area where the crack between the gluteus maximus ends. Further there is an impervious member that is outside of the absorbent pad and greater in area than the absorbent pad.

17 Claims, 8 Drawing Figures

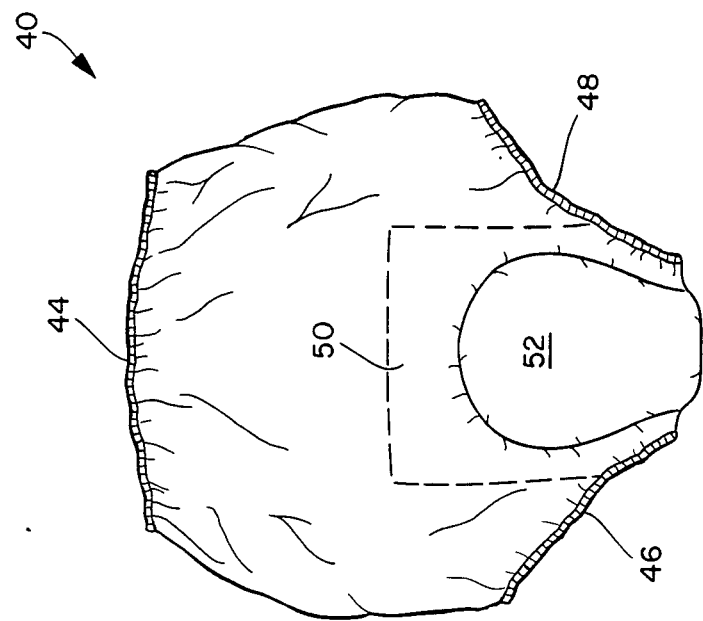
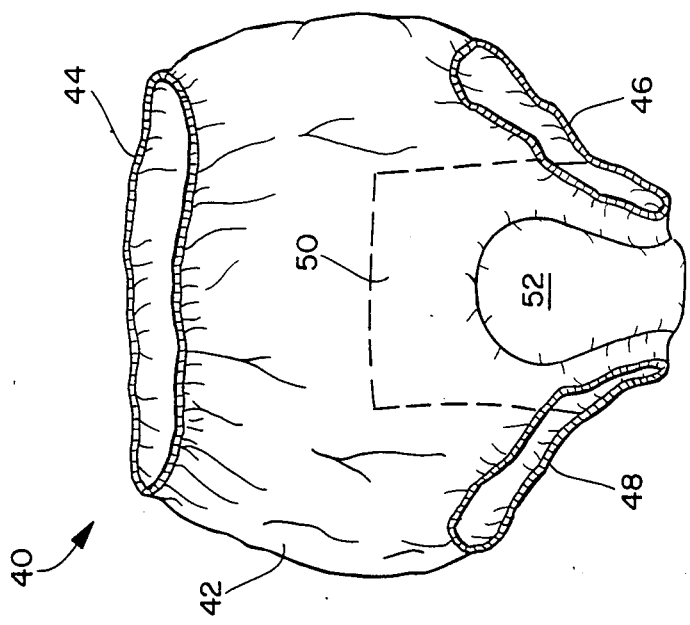
FIG. 3A
FIG. 3

DISPOSABLE LEAKPROOF CATAMENIAL DEVICE

TECHNICAL FIELD

This invention relates to a disposable catamenial or incontinence device comprising a panty-like garment.

PRIOR ART

There have been a variety of garments proposed for use as catamenial devices. These include pads held in place by adhesive connection to underwear, pads held in place by belts and tampon devices. Of particular interest in regard to the invention are those devices that combined a catamenial device with a garment and particularly devices provided for overnight protection.

U.S. Pat. No. 2,748,772—Titone et al. discloses a disposable panty with a pocket to hold a sanitary napkin. The panty further is provided with a plastic barrier in the crotch.

U.S. Pat. No. 3,608,551—Seijo provides a panty that is designed to hold a sanitary napkin closely against the body by means of an elastic. Another panty-like garment having a pocket for holding a replaceable menstrual pad is U.S. Pat. No. 3,599,638—Rickard and U.S. Pat. No. 4,044,769—Papajohn.

Absorbent garments for training infants or for use by adults or children have also been proposed in panty shape such as in U.S. Pat. No. 4,205,679—Repke et al.

However, there remains a need for a catamenial garment, also suitable for mild incontinence, that would provide protection during the heavy flow days of the menstrual cycle, particularly when the wearer is sleeping. When the wearer is sleeping, the movement of the body is likely to dislocate the pad, leading to leakage. Further, there is likely to be heavier volume flow between changings at night. Therefore, there remains a need for an overnight garment that protects effectively against leakage of menstrual fluids.

DISCLOSURE OF THE INVENTION

An object of this invention is to overcome disadvantages of prior devices.

An additional object of this invention is to provide a device that virtually prevents leakage of menstrual fluids in overnight use.

Another object of this invention is to provide a comfortable menstrual or light incontinence panty.

An additional object of this invention is to provide a low-cost menstrual panty-like garment.

A further additional object of the invention is to provide a comfortable overnight feminine garment.

These and other objects of the invention are generally accomplished by providing a panty-like garment containing an integral menstrual pad. The absorbent pad portion extends from the crotch region up in both the back and the front to a point higher than normal menstrual pads. The pad extends at least up to the area where the crack between the gluteus maximus ends. Further there is an impervious member that is outside of the absorbent pad and greater in area than the absorbent garment.

In the preferred form, the panty further is provided with a flap section in the crotch area between the edge of the pad and the elasticized garment leg. In the most preferred embodiment, the elasticized area of the panty leg is provided with much greater elasticity in the outer leg portion than in the portion in the crotch adjacent the pad.

BRIEF DESCRIPTION OF THE DRAWINGS

FIG. 3 is a front view of an alternate garment in accordance with the invention.

FIG. 3A is a rear view of an alternate garment in accordance with the invention.

MODES FOR CARRYING OUT THE INVENTION

The invention has numerous advantages over prior catamenial devices in that it virtually prevents leakage when used overnight, even during the heaviest flow periods of the menstrual cycle. Further, the garment is more comfortable versus a pad or a pad fastened into a panty. Another advantage is that it looks like a panty and therefore is more acceptable to the wearer. The absorbent pad being integral with the panty provides less deformation of the pad when worn than a pad separately fastened in the panty. The garment of the invention also has a lower cost than the combination of a pad and panties when the extra washing of bedding and underclothes is considered as necessary with the leakage of normal catamenial devices. Other advantages of the device will be apparent from the detailed description of the drawings below.

Figure 1:
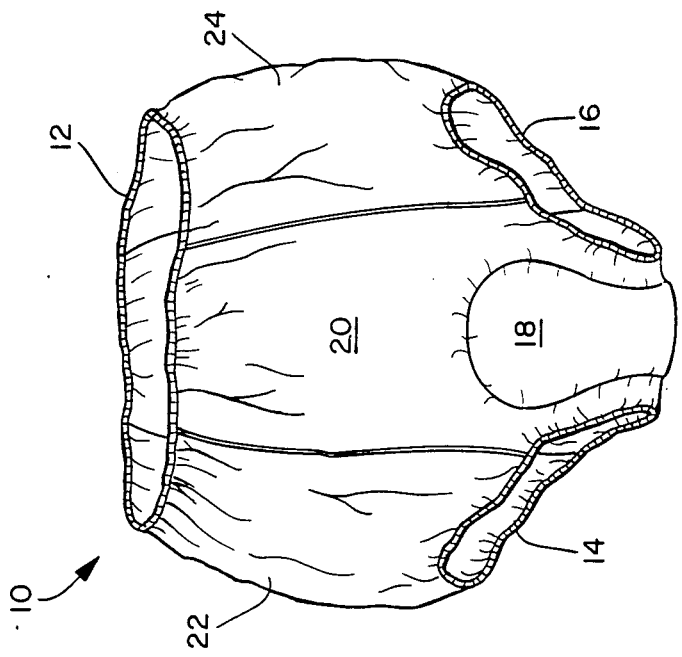
FIG. 1 is a front view of a garment in accordance with the invention.

FIG. 1 illustrates a garment 10 in accordance with the invention. The garment 10 viewed in front view in FIG. 1 has an elastic waist 12 as well as elasticized legs 14 and 16. The garment is provided with a pad 18 that extends high in the front. The panty-like garment is provided with a front panel 20 that is impervious, but may be provided with a cloth covering on the interior, exterior or both. The side portions 22 and 24 that are of a stretchy material that will conform to the body of the wearer.

Figure 2:
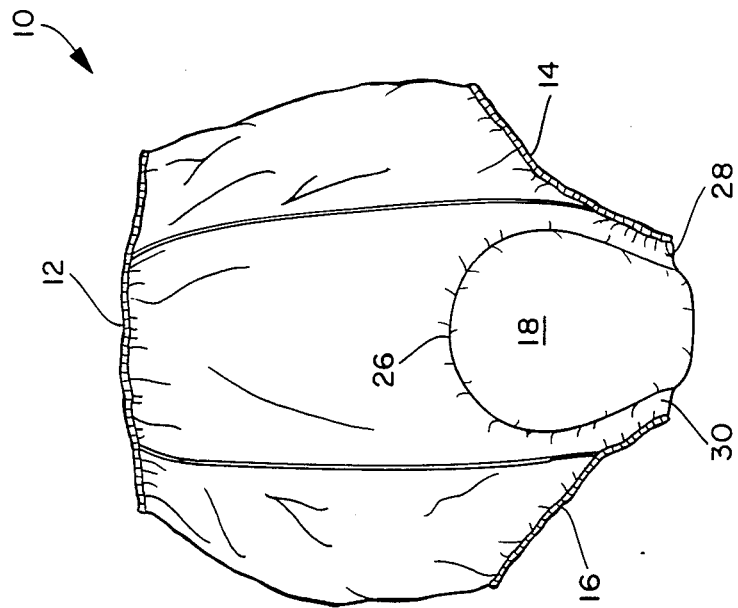
FIG. 2 is a rear view of a garment in accordance with the invention.

FIG. 2 is a back view of garment 10 that illustrates that in the preferred embodiment, the absorbent member 18 extends a point 26 higher than in the front. This point generally corresponds to the upper level of the crack between the buttocks or gluteus maximus. It is noted that there are flaps 28 and 30 that are located between the area of the elastics 14 and 16 of the legs and the pad 18. These areas 28 and 30 are also impervious, but are not covered by the absorbent material.

FIG. 3 illustrates another embodiment in accordance with the invention of garment 40 in the front view of FIG. 3, and rear view of FIG. 3A. The garment 40 that does not have as large an impervious area as garment 10 of FIGS. 1 and 2. In some instances it may be desirable to have such a smaller impervious area in order to form a garment that is not so warm when worn. In garment 40 the entire fabric 42 may be formed of a stretchable material such as ordinarily used in panties. The garment has an elastic waist 44 and elastic legs 46 and 48. The garment 40 is provided with an impermeable area 50 extending to an area larger than the absorbent pad 52. It is again noted that the pad extends further up in the back than in the front.

Figure 5:
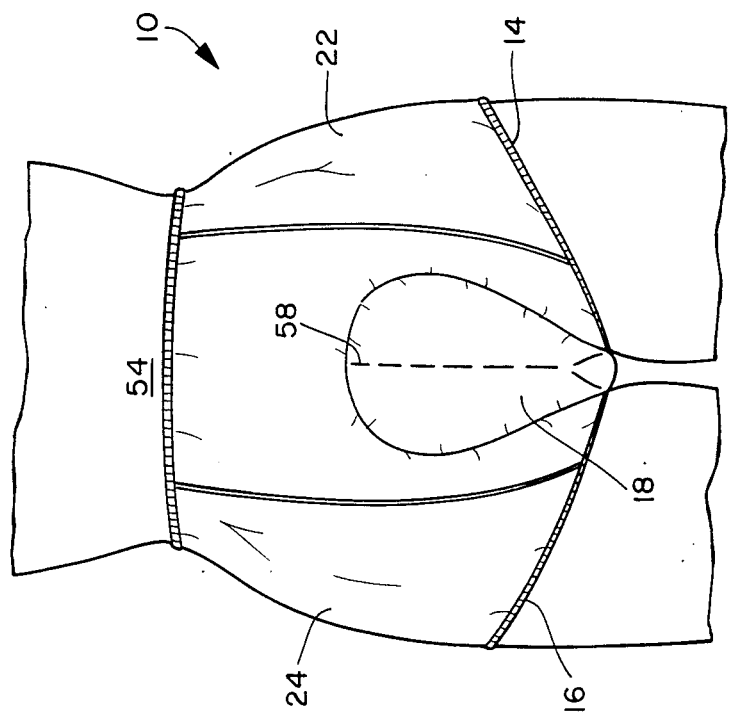
FIGS. 4, 5 and 6 are front, rear and side views of a garment in accordance with the invention as it is worn.
Figure 4:
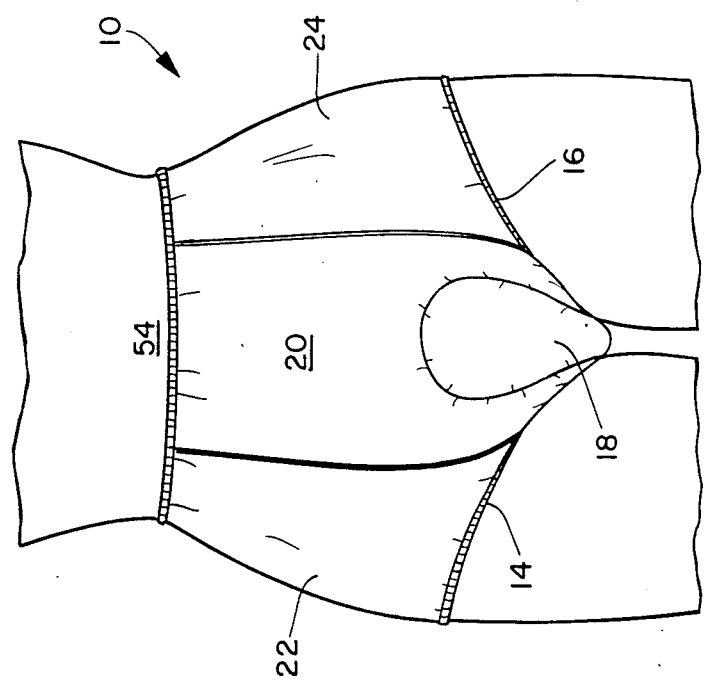
Figure 6:
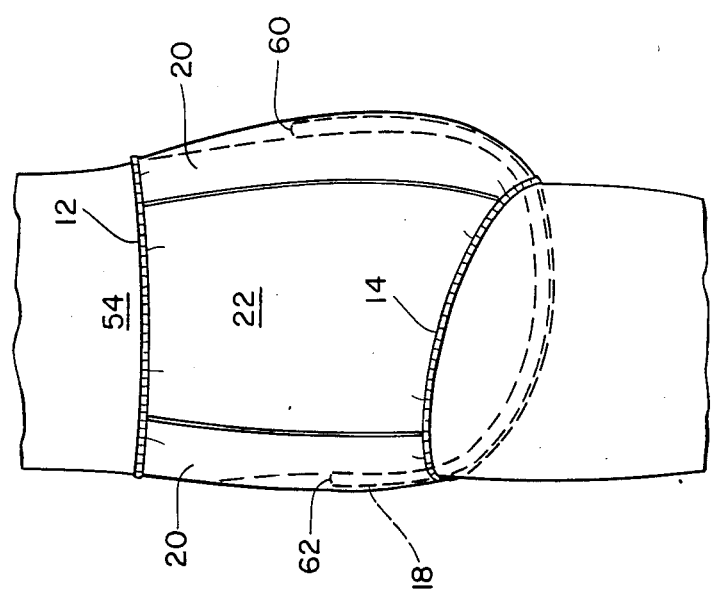

FIGS. 4, 5 and 6 illustrate the preferred garment 10 of the invention when worn. FIG. 4 is a front veiw, FIG. 5 is a back view and FIG. 6 is a side view. The garment 10 fits snuggly at the waist of the wearer 54. The absorbent 18 extends up in the front, at least to the height of the pubic bone. The impervious panel 20 extends to the waist with stretchy portions 22 and 24 extending at the sides from the impervious insert portion 20 that extends from the waist in the front through the crotch to the waist in the back. As viewed in the back, the back portion of the absorbent 18 extends generally to an area 58 at the top portion of the crack between the buttocks or gluteus maximus. It can be seen that the stretchy sides 22 and 24 have conformed to the body. As illustrated in FIG. 6, the upper portion of the rear of the absorbent pad 60 extends further up the body 54 than the upper portion of 62 of pad 18 in the front of the body 54.

Figure 7:
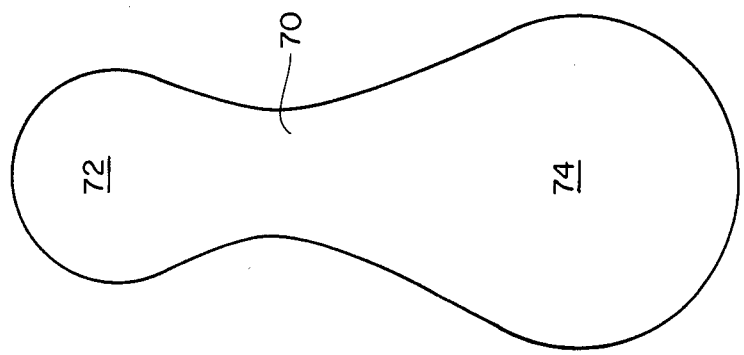
FIG. 7 is a view of the absorbent garment insert of the invention.

Illustrated in FIG. 7 is the general shape of the preferred absorbent of the invention that is composed of a generally bilobal pad having a rear portion or lobe that is both longer in the axial direction and wider in the traverse direction than is the front lobe. The narrower portion 70 is intended to be placed in the crotch with the smaller of the bilobal portions 72 in the front and the larger portion 74 in the rear. The crotch portion may be thicker or contain more highly absorbent materials than the ends of the garment. It is desirable to have a higher absorbency per unit of surface area in the crotch as less surface area is available in the crotch area. Generally the rear is large enough in the axial direction to extend up to about the upper portion of the crack between the gluteus maximus. The smaller front portion will extend to above the pubic area in the front.

The panty of the invention is particularly effective as it has been found that when sleeping, a large portion of leakage of menstrual fluids is from the back. By extending the pad to the terminal portion of the crack between the buttocks, this leakage has been found to be minimized. Further, by using a large permeable cover, the fluids, even if they escape the absorbent portion, do not contaminate the bed clothes of the wearer or the bedding.

The design of the elastic at the legs of the garment has been found to be particularly important. The elastic is designed to fit snuggly but not so tightly as to leave marks on the legs. It has been found particularly preferred that the garment legs be formed with the elastic provided with most of its travel in the outer leg portion of the legs. By providing the major portion of travel in the outer thigh portion and a minor portion on the inner thigh portion, there are less likely to be formed ridges in the crotch portion. Ridges form as contraction of the elastic causes wrinkles as the substrate bearing the elastic is shortened. Such ridges are a site where leakage is more likely. It is generally preferred that the inner portion of the leg elastic be provided with only the ability to stretch to increase by about 5 to about 25 percent of its contracted length to minimize ridge formation. The outer portion is generally provided with enough stretch to stretch to about 35 to about 100 percent longer than its contracted length.

The liquid impervious structure of the panty as set forth in the drawings extends at least to an area larger than the absorbent pad. In a preferred version, the impervious area extends from waist to waist, with the impervious area, therefore, extending from the front waist down through the crotch and up again to the rear waist. The sides then are a stretchable fabric such as a combination of nylon and cotton, typical is panty fabric that is able to stretch at least about to 125 percent of its original size. The impervious materials generally are not stretchable, and the stretch to make the garment form-fitting must come in the stretchable side pieces. However, it is possible that a pervious insert be utilized that does not extend up to the waist in the front and back. It is generally considered that a minimum length of impervious covering would be about 18 inches from the upper portion of the back, extending through the crotch and up into the front above the pubic bone. The length for a garment that extends waist in the front to waist in the back is about 31 inches for a 7 to 8 size garment. The full impervious coverage is preferred for best protection and ease of formation in that only straight seams are required to join the stretchable side portions with the impervious center portions. The width of the impervious portion is generally between about 6 inches and 10 inches, with a width of about 8 inches preferred. The larger the impervious portion, the more likely the garment is to be considered hot as it will not easily pass perspiration.

The garment of the invention may be constructed by placing an absorbent pad on an impervious backing, placing a permeable member over said pad and sealing the impervious member and said permeable member together by ultrasonics in the area where they contact each other outside of the absorbent member; the composite absorbent structure then is bonded to the crotch section of a preformed panty, or if the impermeable member is to form the center portion of the garment, such as in FIGS. 1 and 2, the side cloth pieces are attached and elastic fastened to the legs and waist.

The stretchable side pieces may be formed of any stretchable fabric. Typical of such fabrics are the panty fabrics formed of blends of cotton and nylon that have stretch of greater than 25 percent.

The gasket or flap between the absorbent and the inner leg portion may be of any suitable size that results in effective leakage prevention. Generally suitable sizes are those having a distance between ¼ inch and 1½ inches between the absorbent and the elastic of the panty. It is preferred that the flap be between about ½ and 1 inch to provide a close fit of the absorbent to the labia and to seal well at the thighs. If the distance is too great, the pad will droop from the body, and if the flap is too small, good sealing against leakage will not result.

The amount of absorbent coverage of the body may be any suitable amount that will provide effective overnight protection. It is preferred that the absorbent cover the total pubic area, the crotch and extend in the back to the upper level of the crack between the buttocks. The maximum amount of absorbent extends from the front waist through the crotch and up to the back waist. It is considered that a minimum amount would be about 11 inches for overnight use. The preferred length is between about 12 and 14 inches in length to cover the public area, crotch and extend high enough in the back to prevent leakage. The crotch width of the absorbent generally is between about 2 and about 4 inches for comfort with good leak prevention, although in some instances, absorbents of a width of between 1½ and 6 inches may be utilized. The width of the absorbent in its wider portions in the back and front may be between about 3½ and about 6 inches for good protection from leakage without becoming overall too bulky.

It is possible that the crotch portion of the absorbent material may have a higher absorbency than the ends.

The crotch portion being narrower may be made either thicker or have more highly absorbent materials in order to absorb adequately if the exudate is directed to that area of the pad. Superabsorbents may be utilized to increase absorbency without increasing the thickness of the pad.

The pads for the garment of the invention generally are formed having a body side liner of a nonirritating material that will pass fluids easily. The absorbent materials may be those such as fluff for a low-cost product or coform or microfibers with super absorbent for a product having more absorbency but at somewhat higher cost. The impervious section may be formed of any suitable material. Typical are the polymer films such as polypropylene, polyethylene and blends of ethyl and methyl acrylate. A particularly preferred film has been found to be a composite of polypropylene or ethyl methyl acrylate polymer that has been extruded onto a spunbond material. This is preferred as the spunbond gives a cloth-like look to the outer surface of the garment that prevents the wearer from having the feeling that they are wearing a diaper-like garment rather than a panty.

Generally the total absorbency of the garment is not challenged by the amount of catamenial fluids even for heavy-flow days. The garment has a large amount of absorbency but as the menstrual fluid may flow, either in the front, back or crotch area depending on the body position of the wearer when sleeping, it is necessary to have a higher amount of absorbency in each of these areas in order to always effectively absorb the body exudate. Generally this device will have an absorbency, in water of over 100 cc., even though designed as a catamenial device. This high absorbency also makes the device of the invention suitable for incontinence use.

The device of the invention has been found to be particularly effective. Prior devices, while having sufficient absorbency to absorb catamenial fluids that would be released even in heavy flow days, were not able to provide enough absorbency in the area where the menstrual fluid would appear when the wearer was sleeping. Previous garments also could not protect the wearer when menstrual or urinary flow was at high rates. When the wearer is sleeping, the fluids are likely to be concentrated well towards the back at the rear portion of the crack between the buttocks, in the front at the upper pubic area or in the crotch portion. The catamenial device of the invention provides a large amount of absorbency in each of these areas such that overall protection is provided regardless of the position of the wearer during sleeping. It is found that having the widened portion in the rear presents absorbent to the menstrual fluid even when the wearer's body is deformed in unusual positions during sleep. One cause of failure in catamenial devices during sleep is that the buttocks are deformed as the wearer moves, and the fluid does not contact the pad before the night clothes or bedding of the wearer. The wider portion in the back, combined with the narrow crotch portion and preferably a widened portion in front, prevents this twisting and results in a more effective article.

While the garment of the invention has been particularly described with reference to overnight use for a menstrual garment, it is also within the invention to utilize the garment for incontinence protection. It is particularly desirable for mild incontinence protection as the effective leg sealing will prevent urine leakage, and it may be utilized in overnight use to prevent soiling of bedding.

The garment also could be utilized for wearing after operations that result in leakage from the urinary, vaginal or anus openings. These and other uses are intended to be included by the invention which is only intended to be limited by the scope of the claims attached hereto.

We claim:

1. A disposable undergarment for absorption of human exudate comprising a panty-like garment having an elastic waist, elasticized legs, an absorbent integral with said undergarment extending from at least about the top of the pubic region through the crotch and upward to at least about the point between the upper portion of the crack between the gluteus maximus wherein said garment is provided with an impervious portion extending from a point above the pubic region in the front of the garment and extending through the crotch region and upward in the back to a point above the upper end of the crack between the gluteus maximus of the wearer, wherein there is a greater amount of absorbent in the back of the garment than in the front, wherein the elastic of said elasticized legs is separated from said absorbent by flexible nonabsorbent flaps between the absorbent and said elastic of said elasticized legs and wherein stretchy side fabrics cause said garment to conform to the body of the wearer.

2. the disposable garment of claim 1 wherein th garment is provided with a continuous elastic waist.

3. The garment of claim 1 wherein said impervious portion extends from the pubic region in the front of the garment and through the crotch region and upward in the back to a point at the upper end of the crack between the gluteus maximus of the wearer.

4. The garment of claim 1 wherein said garment has stretchy fabric side portions.

5. The garment of claim 1 wherein said garment is a catamenial device.

6. The garment of claim 1 wherein said garment is a incontinence protection device.

7. the garment of claim 1 wherein said flaps extend between about ½ and 1 inch from said absorbent to the elastic at their outer edge.

8. the garment of claim 1 wherein said liquid impervious portion is greater in area than the absorbent.

9. the garment of claim 1 wherein said absorbent is in a bilobal form with a larger lobe in the rear portion of the garment.

10. The garment of claim 1 wherein said elastic leg portions have a greater elasticity on the outside of each leg than on the inside crotch portion of each leg.

11. The garment of claim 1 wherein said absorbent is between about 11 and about 14 inches in length.

12. The garment of claim 1 wherein the absorbent in the crotch section of said garment has a higher absorbency per unit of surface area than the absorbent in the ends of said garment.

13. The garment of claim 12 wherein said crotch portion of absorbent is thicker than said ends.

14. The garment of claim 8 wherein said impervious backing extends from the front waist down through the crotch and up to the back waist.

15. The garment of claim 1 wherein said flaps are liquid impervious.

16. The garment of claim 1 wherein the sides of said panty-like garment comprise a stretchable panty fabric with a stretch of greater than 25 percent.

17. The garment of claim 10 wherein the stretch of said inside crotch portion is about 5 to about 25 percent of its contracted length and elasticity of said outside of each leg is about 35 to about 100 percent longer than contracted length.

* * * * *